(12) United States Patent
Boey et al.

(10) Patent No.: US 9,486,302 B2
(45) Date of Patent: Nov. 8, 2016

(54) MULTI-LAYERED SURGICAL PROSTHESIS

(71) Applicant: NANYANG TECHNOLOGICAL UNIVERSITY, Singapore (SG)

(72) Inventors: Yin Chiang Freddy Boey, Singapore (SG); Zheng Wang, Singapore (SG); Joseph Tang, Hong Kong (CN)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 412 days.

(21) Appl. No.: 14/059,231

(22) Filed: Oct. 21, 2013

(65) Prior Publication Data
US 2014/0044861 A1 Feb. 13, 2014

Related U.S. Application Data

(62) Division of application No. 13/143,923, filed as application No. PCT/SG2010/000046 on Feb. 10, 2010.

(60) Provisional application No. 61/151,616, filed on Feb. 11, 2009.

(51) Int. Cl.
*A61F 2/00* (2006.01)
*A61L 27/34* (2006.01)
(Continued)

(52) U.S. Cl.
CPC .............. *A61F 2/0063* (2013.01); *A61L 27/34* (2013.01); *A61L 27/56* (2013.01); *A61L 31/048* (2013.01); *A61L 31/10* (2013.01); *A61L 31/146* (2013.01); *B32B 3/266* (2013.01); *B32B 3/30* (2013.01); *B32B 5/142* (2013.01); *B32B 9/02* (2013.01); *B32B 9/04* (2013.01); *B32B 9/045* (2013.01); *B32B 27/08* (2013.01); *B32B 27/16* (2013.01); *B32B 27/18* (2013.01); *B32B 27/302* (2013.01); *B32B 27/304* (2013.01); *B32B 27/308* (2013.01); *B32B 27/32* (2013.01); *B32B 27/322* (2013.01); *B32B 27/34* (2013.01); *B32B 27/36* (2013.01); *B32B 27/40* (2013.01); *A61F 2/2481* (2013.01); *A61F 2250/0031* (2013.01); *A61F 2250/0067* (2013.01); *B32B 2255/10* (2013.01); *B32B 2255/26* (2013.01); *B32B 2264/02* (2013.01); *B32B 2264/10* (2013.01); *B32B 2270/00* (2013.01); *B32B 2307/538* (2013.01);
(Continued)

(58) Field of Classification Search
None
See application file for complete search history.

(56) References Cited

U.S. PATENT DOCUMENTS 3,054,406 A 9/1962 Usher
5,433,996 A 7/1995 Kranzler et al.
(Continued)

FOREIGN PATENT DOCUMENTS

CA 2 443 505 A1 10/2002
EP 1 649 828 A1 4/2006
(Continued)

*Primary Examiner* — Monica Huson
(74) *Attorney, Agent, or Firm* — Seed IP Law Group LLP

(57) ABSTRACT

The present invention generally relates to the field of prostheses for surgical applications, to methods of their manufacturing and to methods of treating a patient by implanting them into a patient. More particularly, the present invention relates to prostheses having a multi-layered sheet structure and their use in hernia repair, the repair of anatomical defects of the abdominal wall, diaphragm, and chest wall, correction of defects in the genitourinary system, and repair of traumatically damaged organs such as the spleen, liver or kidney.

28 Claims, 7 Drawing Sheets

(51) Int. Cl.

| | | |
|---|---|---|
| *A61L 27/56* | (2006.01) | |
| *A61L 31/10* | (2006.01) | |
| *A61L 31/14* | (2006.01) | |
| *B32B 27/08* | (2006.01) | |
| *B32B 5/14* | (2006.01) | |
| *B32B 9/02* | (2006.01) | |
| *B32B 9/04* | (2006.01) | |
| *B32B 27/16* | (2006.01) | |
| *B32B 27/18* | (2006.01) | |
| *B32B 27/30* | (2006.01) | |
| *B32B 27/32* | (2006.01) | |
| *B32B 27/34* | (2006.01) | |
| *B32B 27/36* | (2006.01) | |
| *B32B 27/40* | (2006.01) | |
| *B32B 3/26* | (2006.01) | |
| *B32B 3/30* | (2006.01) | |
| *A61L 31/04* | (2006.01) | |
| *A61F 2/24* | (2006.01) | |

(52) U.S. Cl.
CPC .... *B32B 2307/546* (2013.01); *B32B 2307/706* (2013.01); *B32B 2307/744* (2013.01); *B32B 2307/746* (2013.01); *B32B 2535/00* (2013.01); *C08L 2201/12* (2013.01)

(56) References Cited

U.S. PATENT DOCUMENTS

| 5,795,584 | A | 8/1998 | Totakura et al. |
|---|---|---|---|
| 6,398,814 | B1 | 6/2002 | Paasimaa et al. |
| 6,726,696 | B1 | 4/2004 | Houser et al. |
| 2003/0204270 | A1 | 10/2003 | Berman et al. |
| 2004/0059356 | A1* | 3/2004 | Gingras .................. A61F 2/105 606/151 |
| 2005/0107870 | A1* | 5/2005 | Wang ...................... A61L 31/10 623/1.44 |
| 2005/0113938 | A1 | 5/2005 | Jamiolkowski et al. |
| 2005/0142163 | A1* | 6/2005 | Hunter ................... A61B 17/11 424/423 |
| 2006/0246105 | A1* | 11/2006 | Molz ....................... A61L 27/34 424/423 |
| 2007/0141112 | A1 | 6/2007 | Falotico et al. |
| 2007/0250147 | A1 | 10/2007 | Walther et al. |
| 2007/0260268 | A1 | 11/2007 | Bartee et al. |
| 2008/0081763 | A1 | 4/2008 | Swetlin et al. |
| 2008/0109017 | A1 | 5/2008 | Herweck et al. |
| 2009/0030526 | A1 | 1/2009 | Sommerich et al. |
| 2009/0069904 | A1 | 3/2009 | Picha |

FOREIGN PATENT DOCUMENTS

| JP | 8-506750 A | 7/1996 |
|---|---|---|
| JP | 11-47171 A | 2/1999 |
| JP | 2000272107 A | 10/2000 |
| JP | 2002072107 A | 3/2002 |
| JP | 2003505191 A | 2/2003 |
| JP | 2003527137 A | 9/2003 |
| JP | 2004321785 A | 11/2004 |
| JP | 2004536544 A | 12/2004 |
| JP | 2005514156 A | 5/2005 |
| JP | 2005525167 A | 8/2005 |
| JP | 2005534404 A | 11/2005 |
| JP | 2006102503 A | 4/2006 |
| JP | 2006334430 A | 12/2006 |
| JP | 2007190369 A | 8/2007 |
| JP | 2008173489 A | 7/2008 |
| JP | 2008534065 A | 8/2008 |
| JP | 2009525832 A | 7/2009 |
| WO | 94/19029 | 9/1994 |
| WO | 94/19029 A1 | 9/1994 |
| WO | 01/08594 | 2/2001 |
| WO | 01/80774 | 11/2001 |
| WO | 01/80774 A1 | 11/2001 |
| WO | 03/059201 A1 | 7/2003 |
| WO | 2004/012627 A1 | 2/2004 |
| WO | 2005/000162 A1 | 1/2005 |
| WO | 2007/039160 A1 | 4/2007 |
| WO | 2007/070141 | 6/2007 |
| WO | 2008/002549 A2 | 1/2008 |
| WO | 2008/023164 | 2/2008 |
| WO | 2008/134305 A2 | 11/2008 |

\* cited by examiner

Figure 1
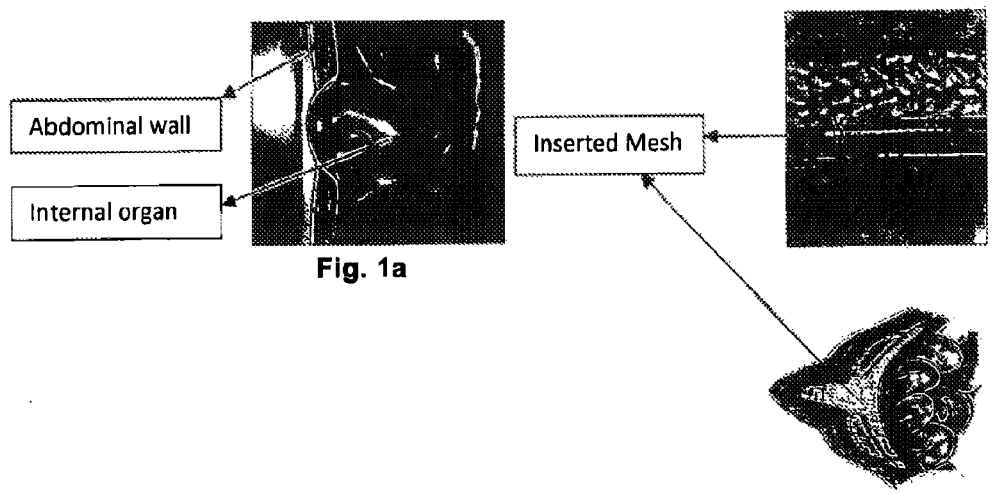
Fig. 1a — Abdominal wall, Internal organ
Fig. 1b — Inserted Mesh
Fig. 1c
Figure 2
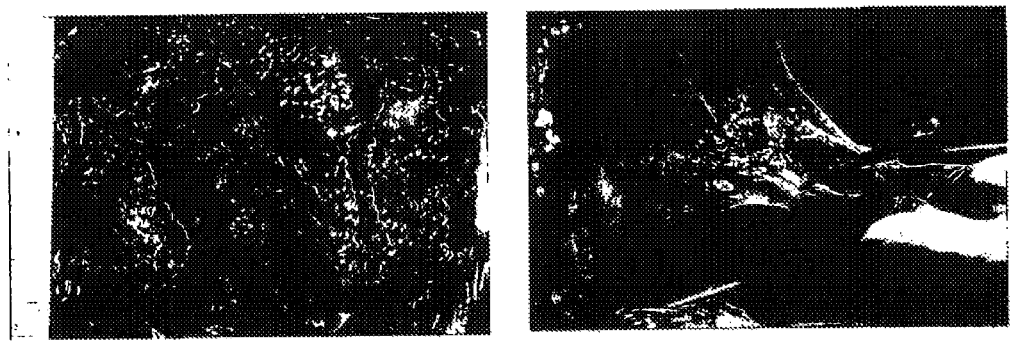

MULTI-LAYERED SURGICAL PROSTHESIS

BACKGROUND

1. Technical Field of the Invention

The present invention generally relates to the field of prostheses for surgical applications, to methods of their manufacturing and to methods of treating a patient by implanting them into a patient. More particularly, the present invention relates to prostheses having a multi-layered sheet structure and their use in hernia repair, the repair of anatomical defects of the abdominal wall, diaphragm, and chest wall, correction of defects in the genitourinary system, and repair of traumatically damaged organs such as the spleen, liver or kidney.

2. Description of the Related Art

Abdominal wall repairs and especially hernia repair are among the most common surgical operations in the United States. A hernia occurs when the inside layers of the abdominal wall weaken and then bulge or tear, causing the abdomen lining to push through the weakened area to form a balloon-like sac. The intestines or abdominal tissue slips into the sac, causing pain and risk of damage. Small hernias can be repaired with sutures but larger hernias are treated by surgically inserting mesh prosthesis into the peritoneum (the membrane separating the body organs from the muscles and fat layers) and securing it in place with sutures or tacks. The prosthesis is usually inserted into an intra-peritoneal location to reinforce the weakened abdominal wall to prevent the balloon sac. FIG. 1 shows an example of a hernia defect and the placement of a mesh to rectify the hernia defect.

Similar mesh prostheses are commonly also used in other surgical procedures including the repair of anatomical defects of the several walls or diaphragms, correction of defects in several lumens or in the genitourinary system, and repair of traumatically damaged organs such as internal organs. Thereby, weakened walls can be reinforced or completed by such mesh prostheses. Sometimes, the prostheses are wound around the organ to serve as a reinforcing member. All such prostheses are usually made from a textile material such as mesh fabrics of woven or knitted fibers or filaments. In the last decades, a variety of different materials for the mesh fabrics have been proposed.

Polypropylene (PP) materials have widely been used in meshes for hernia repair since the 1960's. Incremental innovations were introduced along the way. However, to date, polypropylene has remained unsatisfactory. It has poor tensile strength and elongation and suffers from significant aging effects caused by the formation of microcracks in the polypropylene material which drastically reduce its strength and flexibility over time. In the course of implantation, polypropylene also shows some degree of shrinkage. Polypropylene also results in frequent, significant and unacceptable connective tissue adhesion, which invariably leads to inflammation. The degree of tissue connection correlates directly to the degree of inflammation. If the inflammation response is high, this may result in rigid scar plate formation. Connective tissues adhesion can also cause severe discomfort and even medical trauma in the patient and can lead to the necessity for a premature surgical replacement of the mesh. FIG. 2 shows examples of such extensive visceral adhesions surrounding a polypropylene mesh due to which an additional surgical treatment was necessary.

Polytetrafluoroethylene (PTFE) materials were introduced in the early 1990's to separate tissue from the viscera when closing abdominal wounds. PTFE was further adopted as an enabling technology to perform laparoscopic ventral/incisional repair procedures intra-abdominally. There have been material and performance issues associated with PTFE materials used in hernia repair. Most PTFE materials are extruded and made into sheets. These PTFE sheets had been implanted into the body of a patient, i.e., seroma formation, infection, and sheet shrinkage post-implantation. It is widely-known that a PTFE sheet shrinks on average 34% in 10 to 14 days post-implantation. Many of these patients had to be an additional surgery in order to remove the implanted prosthesis due to these complications.

Recently, PVDF has been shown to be fully biocompatible and can generally possess high strength and flexibility, which has been shown not to age and change over time. It also has almost no shrinkage when used over time, and has significantly smaller tissue adhesion issues. Thus, it has been proposed as a suitable material in textile-based meshes for surgical applications.

In the light of the above experience with sheet-like materials, most of the current hernia meshes are made from filaments woven into a mesh. While easy to produce by weaving, such a process limits the design possibilities of the mesh. For example, based on the anatomical characteristics of the human abdomen, an optimally compatible mesh should have a higher degree of stretch and flexibility in one direction over the other perpendicular direction. This is not easily achieved using a filament weaving process. Also, when stretched, such a filament woven mesh would undergo a reduction of pore size of its open cells or pores (the space between the filaments). It is known that such a reduction of pore size would also detrimentally increase the likelihood of visceral tissue adhesion. However, despite of these disadvantages of woven meshes, the common prostheses used in connection with hernia repairs are made of different textile materials such as mesh fabrics. Examples of such mesh fabrics are disclosed in US Patent Application No. 2007/0250147 A1. Knitted and woven fabrics constructed from a variety of synthetic fibers and the use of the fabrics in surgical repair is also known (e.g., U.S. Pat. No. 3,054,406).

There are two key problems still unresolved in current prosthesis such as prosthesis for hernia repair. One is the undesired viscera tissue adhesion to the prosthesis, i.e., the adhesion of the organs inside the abdomen to the prosthesis, coming as a response to the surgical procedure, and inflammation caused by the prosthesis to the peritoneum. The occurrence is very high with existing prosthesis such as the above-described hernia meshes and results in severe continuous pain, immobility and bowel related problems. Approximately above 30% of the patients require re-surgery due to this adhesion phenomenon. The other key problem is that the mechanical behavior of the current prostheses changes adversely over time due to polymer swelling and/or aging, resulting in poor flexibility and strength. Over time, the prosthesis stiffens and no longer flex in compliance to the abdominal wall movements in any directions, causing very poor anchoring and compliance. Often, the prosthesis would completely break and need urgent surgical replacement.

It is therefore an object of the present invention to provide a prosthesis that overcomes some of the above explained difficulties.

BRIEF SUMMARY

According to a first aspect of the present invention, a prosthesis having a multi-layered sheet structure is provided. The multi-layered sheet structure comprises at least two continuous polymer film layers.

According to a further aspect of the invention, a method of manufacturing a prosthesis having a multi-layered sheet structure is provided. The method comprises forming at least two continuous film layers to produce the multi-layered structure.

In another aspect the present invention provides a method of treating a patient in need of a sheet-like surgical prosthesis or a patient in need of hernia repair, a repair of anatomical defects of the abdominal wall, diaphragm, or chest wall, a correction of defects in the genitourinary system, or a repair of traumatically damaged organs such as the spleen, liver or kidney, and the like. The method includes the implantation of the prosthesis of the invention into the patient in need thereof.

Further embodiments are described in the dependent claims. Further aspects and features of the invention will also become apparent from the following description of specific embodiments and non-limiting examples of the present invention as well as from the attached drawings. It is to be understood that the exemplified embodiments and the drawings are designed for the purpose of illustration only and are not intended as a definition of the limits of the invention.

BRIEF DESCRIPTION OF THE SEVERAL VIEWS OF THE DRAWINGS

The present invention will be better understood with reference to the detailed description when considered in conjunction with the non-limiting examples and the accompanying drawings.

FIG. 1 is an illustration of a hernia defect and a hernia repair by using a mesh-like prosthesis, wherein FIG. 1a shows a hernia defect resulting from a weakened abdominal wall, FIG. 1b shows an inserted mesh placed into and fixed in the peritoneum, and FIG. 1 c shows an exploded view before closing the peritoneum.

FIG. 2 shows photos of two meshes that have adhered onto the viscera.

DETAILED DESCRIPTION

Figure 3:
FIG. 3 shows a cross-sectional view of a two-layered prosthesis of the invention comprising a porous layer 10 and a reinforcing layer 20.

The novel prosthesis according to the first aspect of the invention has a multi-layered sheet structure comprising at least two continuous polymer film layers.

The term "prosthesis" as used in the present invention means any sheet-like structure which can be a substantially flat sheet made of at least two layers, i.e., two, three, four, five or more consecutive layers of sheet-like format, layered or arranged on each other. Such a substantially flat sheet is often called a two-dimensional structure, even though each sheet has a specific thickness. However, the thickness of the sheet is usually small and is generally not considered as a third dimension. Hence, the term sheet as used to define the main structure of the prosthesis referred to herein is defined to be a body having a shape which substantially extends within a plane (two dimensions), e.g., a patch or foil. Nevertheless, the sheet structure is not limited to a two-dimensionally one, and bodies having a three-dimensional sub-structure with a complex shape also fall within the definition of the term prosthesis, if at least the main body (more than about 50% such as 55%, 60%, 65%, 70%, 75, 80% or more of the total body) of the prosthesis has a sheet-like structure. For example, the three-dimensional sub-structure can comprise a plug on a multi-layered sheet made of the same or any different material. Such a plug may be used to bridge a gap between two tissues, e.g., if the wound or defect to be closed is too broad to be closed without any synthetic material or not enough tissue is present to close the gap. Another example for such a three-dimensional sub-structure may be an artificial opening(s), such as a stoma or barriers isolating, e.g., blood vessels or spermatic cords from adhering to the prosthesis. A further example can be a projecting guiding cone to facilitate placement of the prosthesis at the exact center of the abdomen using a long straight needle through the skin and hernia sac.

The prosthesis may be configured to have any suitable shape as long as it is relatively flat (i.e., extends substantially in two dimensions) and sufficiently pliable to allow a surgeon to manipulate the shape of the surgical prosthesis to conform to the anatomical site of interest and to be sutured or stapled thereto. The outline and the size of the prosthesis may vary according to the surgical application as would be apparent to one of skill in the art. The prosthesis can be pre-shaped or shaped by the surgeon during the surgical procedure. To be sufficiently moldable during implantation, the prosthesis can be substantially flexible along its longitudinal axis (longitudinal axis in this respect means the main axis or the main longitudinal extension) of the prosthesis. In case of a square-like contour of the prosthesis, the longitudinal axis, for example, can be the x or y axis, if the square body extends within the x-y-plane.

The prosthesis described herein can be used for implantation in mammals (such as a human, dog, cat, rabbit, mouse, rat, etc.) in need thereof. Especially, the prosthesis can be used for treating any wall defect or damaged organ, but is not limited thereto. Various examples of wall defects are hernia defects, anatomical defects of the abdominal wall, diaphragm and/or chest wall, or defects in the genitourinary system. Various examples of damaged organs which can be treated, for example, by winding the sheet-like prosthesis around the damaged organ or implanting it into the wall of the damaged organ for reinforcing it, include internal organs such as the spleen, liver, kidney, lung, bladder or heart, or organs of the intestinal tract, such as the stomach or the bowel. Illustrative examples of a prosthesis described herein are heart patches, colonic patches, vascular prosthesis like vascular patches, patches for wound healing like suture patches or meshes, hernia patches, gastrointestinal prosthesis like prosthesis for the mouth, pharynx, esophagus, stomach, small intestine, large intestine, rectum, and anus, patches for the urogenital system and the like.

In the present context, the term "continuous polymer film layer" particularly refers to a layer made from a polymeric material in the form of a continuous film. Such a continuous film can be made by any known method as long as the polymer film is integrally formed or molded, i.e., formed into a one-piece film. In other words, the continuous polymer film layer used herein is usually made from a liquid or paste-like polymer material, followed from hardening the material to generate a continuous polymer film in a specific form. In contrast to the continuous film layers described herein, a woven or knitted textile mesh made of a layer of woven or knitted polymer fibers (i.e., re-shaped or trans-formed fibers) does not have a "continuous" polymer film structure as defined above. The reason is that such a textile layer includes several distinguished filaments or fibers within the layer having solid/solid boundaries between each other. Thus, they do not form a continuous, integrally formed polymer film. Nevertheless, it is within the meaning of the term "continuous" as defined in the present invention that the polymer film can comprise pores or through-holes which are prepared either during the manufacturing of the polymer film layer, e.g., by casting, molding, etc., or after its manufacturing, e.g., by mechanical abrasion, cutting, etc., of the hardened polymer material at the desired region in order to form a porous or mesh-like structure.

The layer thickness of each of the layers of the multi-layered sheet structure can be specifically adjusted in view of the respective mechanical or physical properties of each of the layers. However, the thickness of each of the layers is generally in the micrometer range, for example, the thickness is in the range of about 1 to about 5000 μm. The layer should not be thicker than about 5000 μm, 4500 μm, 4000 μm, 3500 μm, 3000 μm, 2500 μm, 2000 μm, 1500 μm, 1000 μm, 750 μm, 500 μm, 400 μm, or 300 μm, however, the prosthesis should have an essentially sheet-like shape in order to provide flexibility sufficient for the application in the respective treatment methods or the applications of the prosthesis of the invention. Especially, if the overall thickness of the multi-layered prosthesis will be too high, the flexibility will generally be so low that the prosthesis cannot be adequately anchored to the surrounding tissue, while being able to flexibly and elastically stretch along with the tissue. The lower limit of each of the layers should be about 1, 2, 3, 4, 5, 10, 15, 20, 25, 50, or 100 μm in order to provide enough burst strength to the prosthesis of the invention. Each layer can have a thickness in the above-mentioned range or can have a varying thickness within this range.

The polymer material can be any polymer material including oligomers (e.g., from 2 to 5 to 10 to about 25 copies of one or more constitutional units, commonly referred to as monomers) or homopolymers and/or copolymers (e.g., from about 25 to 50 to 100 to 250 to 500 to about 1000 or more copies of one or more constitutional units, commonly referred to as monomers) of for instance a biocompatible and/or bioresorbable polymer material. The polymers may take one or more architectures, which may be selected, for example, from linear, cyclic, and branched including dendritic architectures, among others. Where copolymers are used, the at least two constitutional units can be arranged randomly, periodic, or block-like, etc.

As defined herein, a "biocompatible" polymer material refers to a polymer material with minimal toxicity or irritation to biological tissue. Thus, it is sufficiently tolerated by the body without adverse effects. Such a biocompatible polymer material can be a biostable component for a long-term use, i.e., a component which essentially remains intact over the period that the prosthesis is intended to remain implanted in the body. A "bioresorbable" polymer material is defined to be one which does not remain intact over the period that the prosthesis is intended to remain within the body, for example, due to dissolution, chemical breakdown, etc., of the components. In other words, a bioresorbable material is readily susceptible to biological processing in vivo. It can be degraded by a living organism or a part thereof (e.g., bacterial or enzymatic action) or by the impact of the ambience, such as exposure to radiation, such as visible light, moisture, elevated temperature and/or air, etc., Degradation of a bioresorbable material may result in the formation of primary degradation products such as compounds of low molecular weight, which then decay further through the action of living organism. In the present context, the term "bioresorbable material" particularly refers to a material that can be completely removed from a localized area, by physiological metabolic processes. A bioresorbable compound can, when taken up by a cell, be broken down into components by cellular machinery, such as lysosomes or by hydrolysis, so that the cells can either reuse or dispose of without significant toxic effect to the cells. Examples of biodegradation processes include enzymatic and non-enzymatic hydrolysis, oxidation and reduction. Suitable conditions for non-enzymatic hydrolysis, for example, include exposure of bioresorbable material to water at a certain temperature and a pH of a lysosome (i.e., the intracellular organelle). The degradation fragments typically induce no or little organ or cell overload or pathological processes caused by such overload or other adverse effects in vivo.

The biocompatible polymer material which can be used in the porous layer of a prosthesis described herein is not specifically restricted and any biocompatible material known in the art which is suitable for prosthesis can be used. Examples for biocompatible polymer materials can include, but are not limited to, a synthetic polymer including oligomers, homopolymers, and copolymers resulting from either addition or condensation polymerization. Various examples of suitable addition polymers include, but are not limited to, acrylics such as those polymerized from methyl cerylate, methyl methacrylate, acrylic acid, methacrylic acid, acrylamide, hydroxyacrylate, hydroxyethyl acrylate, hydroxyethyl methacrylate, glyceryl acrylate, glyceryl methacrylate, methacrylamide and ethacrylamide; vinyls such as styrene, vinyl chloride, polyvinyl alcohol, polyvinylidene fluoride and vinyl acetate; polymers formed of ethylene, propylene, and tetrafluoroethylene, or any polymer blends, copolymers, or derivatives thereof. Various examples of condensation polymers include, but are not limited to, nylons such polycaprolactam or polylauryl lactam; polyurethanes, polycarbonates, polyamides, polysulfons, and poly(ethylene terephtalate). Illustrative examples of such biocompatible polymer materials include, but are not limited to polyvinylidene fluoride, polyamide, polyethylene, polypropylene, poly(ethylene terephtalate), polyurethane, polystyrene, polymethacrylate, polytetrafluoroethylene, and polymers or copolymers of p-dioxanone, trimethylene carbonate (1,3-dioxan-2-one) and alkyl derivatives thereof, valerolactone, butyrolactone, decalactone, hydroxybutyrate, hydroxyvalerate, 1,5-dioxepan-2-one, 1,4-dioxepan-2-one, 6,6-dimethyl-1,4-dioxan-2-one, or any polymer blend thereof.

Various examples of bioresorbable polymer materials are known in the art, any one of which is generally suitable for use in a polymer coating described herein. Examples of bioresorbable polymer materials that are considered bioresorbable include, but are not limited to polydioxanone, polygluconate, polylactic acid-polyethylene oxide copolymers, polysaccharides, cellulose derivatives, hyaluronic acid based polymers, polyhydroxybutyrate, polyanhydride, polyphosphoester, poly(amino acids), aliphatic polyesters, biodegradable polyethers, poly(amino acids), copoly(ether-esters) such as PEO/PLA dextran, polyalkylenes polyoxalates, polyamides, polyketals, poly(iminocarbonates), polyorthoesters, polyoxaesters, polyamidoesters, polyoxaesters containing amido groups, poly(anhydrides), polcyanoacrylates, poly(alkyl cyanoacrylates), poly(alkyl fumarates) like poly(propylene fumarate), polyphosphazenes, polycarbonates, naturally-occurring biodegradable polymers such as chitosan, starch, gelatin, collagen, fibrinogen, fibrin, cellulose, alginate, polysaccharides, amylase, or any polymer blends, copolymers, or derivatives thereof. Examples of polyorthoesters include a polyglycolide, a polylactide, a poly-co-glycolactide, a polylactic acid, a polyglycolic acid, a poly(ethylene glycolide), poly(ethylene glycol), poly(ethylene glycol) diacrylate, a polyalkylene polymer like polyethylene succinate or polybutylene diglycolate, a polyhydroxybutyrate, polyhydroxyvalerate, a polyhydroxybutyrate/polyhydroxyvalerate copolymer, polyhydroxyalkoate, a polyanhydride, an aliphatic polycarbonate, a polycaprolactone like poly(ε-caprolactone), a biodegradable polyamide, a biodegradable aliphatic polyester, and/or copolymers thereof. Illustrative examples of biodegradable polymers include, but are not limited to a polylactide, such as poly(L-lactide) (PLLA), a polycaprolactone (PCL), a copolymer of poly-caprolactone (PCL) and polylactic acid (PLA), or a copolymer of poly(lactide) and poly(glycolide) (PLGA). More specific examples of copolymers which can be used include, but are not limited to copolymers of a poly(lactide) and a poly(glycolide) (PLGA) having an glycolide content of about 5-50%, 10-50%, 15-50%, or 20-50%, or approximately 20%, 25%, 30%, 35%, or 50%, based on the copolymer composition. Each of the above-mentioned bioresorbable polymer materials has a characteristic degradation rate in the body. For example, PGA and polydioxanone are relatively fast-bioabsorbing materials and degrade usually in the range of weeks to months. PLLA and polycaprolactone are examples for relatively slow-bioabsorbing materials and degrade usually in the range of months to years. Thus, one skilled in the art will be able to choose an appropriate bioresorbable material with a desired degradation rate that is suitable for the desired application of the prosthesis.

In some embodiments, a porous layer can be provided as one of the layers in the multi-layered sheet structure of the prosthesis described herein. The porous layer can be made of any one of the above-mentioned polymer materials such as a biocompatible or bioresorbable material. A "porous structure" refers to a layer having pores at least within the outer part or the surface area of the layer or having pores within the whole layer. "Pores" means any regular or irregular shaped pores (e.g., short channels or cavities (e.g., having a depth of about 10 to about 500 μm, but at least about 10 μm, 20 μm, 30 μm, 40 μm, 50 μm, 75 μm, or 100 μm and not more than about 200 μm, 250 μm, 300 μm, 350 μm, 400 μm, 450 μm, or 500 μm) in the surface area of the layer, which are also called "wells" or "pot holes", or spherically or non-spherically shaped holes within the layer). Such pores or cavities in the surface layer result in a so-called "rough" surface. Roughed surface means that the surface texture consists of pores as defined herein. The term "pores" also refers to through holes (e.g., having the same depth as defined above, but which extends through the whole porous layer). Such through holes can extend from the upper surface of the porous layer to the inner part thereof in a uniform (e.g., having a cuboid or pillar-like structure), tapered (e.g., having a regular or irregular conical or step-wise tapered shape) or irregular (e.g., having a bent or meandered shape) manner. In addition, through holes may also extend not only through the porous layer, but also through two or more layers, e.g., throughout all layers, of the prosthesis. That means that the pores may be through holes extending within the porous layer only or extending through the whole prosthesis, thereby forming micro-channels within the prosthesis. Generally, the extension direction of the pores or through-holes is substantially perpendicular to the extension of the plane of the sheet. In case the through holes extend from the upper surface of the prosthesis to the opposite surface of the prosthesis, the prosthesis is sometimes called to be a perforated sheet or a mesh-like sheet.

The delimiting walls of the pores or the through holes are defined by at least a pair of opposing lateral surfaces and optionally a base surface. The term "surface" may be understood as referring to a flat or a curved area, which may be of any desired geometry. The distance between the two opposing lateral surfaces of at least a portion or the entire of the pores or through holes is within the micrometer range. As used herein, the term micrometer range refers to a range of between about 1 to 10000 μm. The surfaces of the pores may be of any desired internal surface characteristic and any desired material as long as they allow cells or tissue of a desired type to grow therein. Various embodiments of specific surface characteristics include one or more steps, dents, inversions, bulges, grooves, or striations. However, in some embodiments, the surface can be of any uniform topology, for example, at least substantially flat or at least essentially complanate, including having an at least essentially straight surface.

Furthermore, different areas of the surfaces of the pores may provide different surface characteristics and include or consist of different materials, e.g., where the pores extend within two or more different polymer film layers of the multi-layered structure. This allows that the tendency of the tissue to grow in or through the pores can be differently adjusted within one pore or through hole.

According to the invention, the pores or through-holes may have any desired shape, including a straight, bent, or meandering (or otherwise winding) shape and may include one or more bends, kinks or branches as long as tissue can be grow in or grow through the pores. In typical embodiments the pores or through holes have one longitudinal axis. The pores may possess a cross section of any desired profile, such as being a regular like a polygonal, cuboid (e.g., with rectangular, rhomb-like or square profile) or alternatively a circle-like structure or any other suitable irregular profile having a desired irregular and/or convoluted cross section. In some embodiments the irregular profile of the pores is a profile which cannot be prepared by weaving or knitting, but which can be manufactured by using mechanical abrading or cutting methods such as stamping, grinding, laser cutting and the like. In the context of the present invention, such an irregular shape like a non-circular or monosymmetric shape is also called "anisotropic shape" of the pores or through-holes. "Anisotropic" in this context also means that the pore shape is irregular, e.g., non-circular or monosymmetric, or the pore structure within the layer is irregular either in the plane view or its cross-section (i.e., a monosymmetric structure which is, e.g., formed of pores with various pore shapes or various pore sizes or pores being non-uniformly distributed).

In some embodiments of the invention, the pores function as means for enabling anchoring of the prosthesis to the abdominal tissues. This anchoring effect results from an enhanced penetration, "growth in" or "growth through" of tissue into the pores of the porous layer or the prosthesis. In addition, a porous surface can also provide a high friction or wettability due to the higher surface area and the capability of retaining fluids. In some embodiments, the friction of a roughed surface, which can for example be prepared by casting on a roughened mold, can for instance be suitably improved by means of a treatment for altering the surface of the pores or the porous layer. Such a treatment may include various means, such as mechanical, thermal, electrical, or chemical means. Various examples of a mechanical treatment suitable for adjusting the desired surface friction and/or surface roughness of the layer include, but are not limited to, a plasma treatment, a sandblasting treatment, an embossing treatment (e.g., by printing a formable paste), or a sizing (or "coining") treatment. As examples of electrical treatments can be given a corona treatment or electrical discharge machining. Various examples of a chemical treatment include a plasma polymerization coating, solution coating or chemical etching. As an illustrative example of a chemical surface treatment for increasing the wettability, it is referred to, for example, a treatment for rendering the surface properties of any hydrophobic surface hydrophilic by coating with a hydrophilic polymer or by treating for instance with surfactants like tris(hydroxymethyl)acrylaminomethane (THAM) or sucrose esters. Further examples of chemical surface treatments include, but are not limited to, exposure to or coating with silanes like trimethylchlorosilane, dimethyl dichlorosilane, propyl trichlorosilane, tetraethoxysilane, glycidoxy propyltrimethoxy silane, 3-aminoproyl triethoxysilanepolydimethylsiloxane; polyacrylates like poly(methyl methacrylate) or poly(ethylmethacrylate) or copolymers with other biocompatible monomers, bioresorbable polymers like poly(glycolic acid), poly(lactic acid) or poly(lactic-co-glycolic acid), adhesion-promoting molecules promoting or encouraging adhesion or attachment of endothelial cells to a surface including endothelial cell growth factors (e.g., platelet-derived ECGF, ECGF-β, ECGF-2a or ECGF-2b), peptides, polypeptides, glycoproteins, proteins like a cell surface protein such as fibronectin, vitronectin, laminin, tenascin, collagen, gelatin, polylysine, synthetic peptides, desirably adhesion peptides having about 3 to about 30 amino acid residues in their amino acid sequences, such as arginine-glycine-aspartate (RGD), arginine-glutamic acid-aspartic acid-valine (REDV), and tyrosine-isoleucine-glycine-serine-arginine (YIGSR), and the like.

The pores can have any pore size as long as their size allows tissue to penetrate, "grow in" the pores or "grow through" the prosthesis during the healing process after the prosthesis has been inserted into a patient. In some embodiments, the average pore size of the pores in the porous layer is about 0.5 to about 5 mm, both limits inclusive. The average pore size, dependent on the site of implantation and the ratio of penetration, growth in or growth through abdominal tissue into the pores. Especially, the lower limit of the average pore size can be about 0.6, 0.7, 0.8, 0.9, 1.0, 1.1, 1.2, 1.3, 1.4 or 1.5 mm. The upper limit of the average pore size can be adjusted to any value between about 2.5 to 5 mm such as about 2.6, 2.7, 2.8, 2.9, 3.0, 3.5, 4.0, 4.5 mm. The term "average pore size" means the average value of the width or diameter of all pores within the respective porous layer. In this respect, methods for measuring the average pore size are known in the art. Illustrative examples are optical microscopy or scanning electron microscopy, but the present invention is not limited thereto.

In some embodiments, the prosthesis having a multi-layered structure has an additional continuous polymer film layer supporting the porous layer. In FIG. 3, an illustrative embodiment of such a two-layered prosthesis is shown in its cross-sectional view. The layer 10 is the above-described porous layer on which the second layer 20, also called reinforcing layer, is provided. The reinforcing layer 20 generally provides a respective reinforcing action to the prosthesis and, thus, allowing a reinforcement of a tissue or closing a tissue or wall defect if none of the other layers of the multi-layered structure has a sufficient reinforcing action. This layer can be made of any polymer material as long as the material has the respective physical properties, such as a burst strength sufficient to ensure that the prosthesis does not break or tear after insertion into a patient and to allow reinforcement or tissue closing. Illustrative examples include, but are not limited to, the above-described biocompatible or bioresorbable polymer materials. In some embodiments, in which the surface of the prosthesis opposite to the porous layer, i.e., the surface facing the visceral organs, is used as reinforcing layer, the layer can also provide an anti-adhesion effect for visceral tissue to avoid any adhesion of the prosthesis to the visceral tissue. This anti-adhesion effect for visceral tissue can be provided for instance either by a relative smoothness of the surface of the support layer, i.e., having no essential pores or pores in the sub-micrometer range, or by comprising a specific polymer material having anti-adhesion properties.

In the light of the above, in case the prosthesis is made of a two-layer structure, the prosthesis is generally implanted into the body of a patient (generally a mammal) such that the outer side of the porous layer faces the abdominal wall and the other side, i.e., the side of the above-mentioned reinforcing layer, faces the visceral organs. Thus, the multi-layered structure of the prosthesis can enable a good anchoring to the abdominal tissues due to the porous structure of the first layer, while the second surface which faces the visceral parts prevent visceral tissue adhesion to the prosthesis. In some embodiments, the anchoring effect to the abdominal tissues can be improved by providing the porous layer with a surface having a high friction or a high wettability as explained above in more detail. In alternative embodiments, however, the surface can be coated with an additional layer providing the respective properties, i.e., a good anchoring effect to the abdominal tissues by means of a high surface friction and/or roughness or a high wettability, etc.

Figure 4:
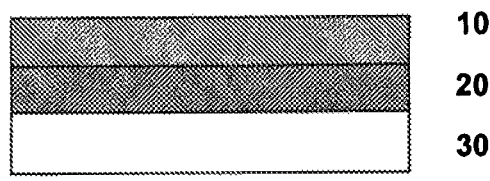
FIG. 4 shows a cross-sectional view of a three-layered prosthesis of the invention comprising a porous layer 10, a reinforcing layer 20, and an anti-adhesion coating layer 30.

The prosthesis of the invention comprises in some embodiments an additional polymer film layer having an anti-adhesion effect for visceral tissues in addition to the above-described first layer enabling an anchoring property to abdominal tissues and the above-described second reinforcing layer. FIG. 4 shows a cross-sectional view of an illustrative embodiment of such a three-layered prosthesis comprising a porous layer 10, a reinforcing layer 20, and an anti-adhesion coating layer 30. In contrast to the illustrative embodiment shown in FIG. 4, where the layer 30 covers the whole layer 20, the anti-adhesion coating layer 30 can be provided as part of one or both outer surface(s) of the prosthesis where the anti-adhesion effect is needed as a barrier to the surrounding organs or tissues.

The term "anti-adhesion coating layer" means that this additional layer provides an anti-adhesion effect to the prosthesis sufficient to prevent any adhesion of organs or tissues, such as visceral tissues on the prosthesis, if a fixation of the prosthesis to these organs or tissues is not desired. Therefore, where adhesion to visceral tissues such as in hernia repair, for example, is not desired, this layer is provided on the side facing the visceral tissue in the body similar as in the two-layered embodiment described above. The anti-adhesion coating layer can generally be made of the same polymer material as the other two layers as long as the material properties, the surface structure of the layer or the additional components of the layer such as additives, fillers, stabilizer, anti-adhesion agents, and the like provide an anti-adhesion effect for visceral tissues. Various examples of the polymers to be used in the anti-adhesion layer are given above.

In addition to the polymer material, the anti-adhesion coating layer may comprise additives such as common additives or filler materials, stabilizer, or anti-adhesion agents. Any anti-adhesion agent known in this field can be used as long as the agent is biocompatible, i.e., for instance is non-toxic or non-irritating. Illustrative examples of anti-adhesion agents which can be used in the anti-adhesion coating layer include, but are not limited to, a carboxymethyl cellulose (CMC), collagen, collage/chitosan mixtures, omega-3 fatty acid, hyaluronic acid, oxidized regenerated cellulose, dextran, pectin, gelatin, polysaccharides, biocompatible surfactants like polyethylene glycols, polypropylene glycols or poloxamers, and derivatives and/or blends from these materials. Collagen and CMC can be crosslinked before being used as anti-adhesion agent.

Figure 5:
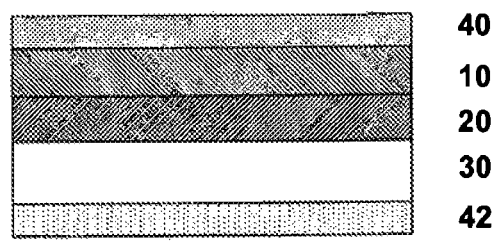
FIG. 5 shows the prosthesis illustrated in FIG. 4 coated on both sides with drug-releasing layers 40 and 42.

In other illustrative embodiments, the above-described prosthesis having a two- or three-layered structure (or a multi-layered structure with three, four or more different layers) is constructed of at least one, two or three drug-releasing layers. That means that the porous layer 10 and/or the reinforcing layer 20 and/or the anti-adhesion coating layer 30 may comprise one or more releasable drugs, therapeutic agents and/or pharmaceutically active substances. In alternative embodiments, the above-described prosthesis is coated with an additional polymeric drug-releasing layer on one or both outermost layers of the prosthesis, comprising one or more releasable drugs, therapeutic agents and/or pharmaceutically active substances. The provision of two additional drug-releasing layers can also be obtained if one or more of the other layers are drug-loaded. FIG. 5 shows an illustrative embodiment of the prosthesis shown in FIG. 4 which is coated on both sides with drug-releasing layers 40 and 42.

In this respect, the additional drug-releasing layers 40 and 42 may be made of any biocompatible or biodegradable polymer material as defined above for the other layers of the multi-layered structure as long as the material has drug-releasing properties. For example, the polymer coating can control the elution of the drug, for example, by adjusting the elution or diffusion rate of the drug. The release of the drug may also be accomplished by controlled degradation of the polymer coating. Where bioresorbable polymer material(s) is/are coated, the polymer coating should be biodegraded within the body after drug elution in order to avoid any deleterious effects which can be associated with decomposition reactions of polymer compounds in vivo. Thus, in these specific embodiments, a bioresorbable polymer material as defined above should be used for the drug releasing layers 40 and 42. In addition, the surface of each drug releasing layer may be surface treated in the same manner as the porous layer 10 or the anti-adhesion coating layer 30 in order to have a similar function as the underlying layers. That means, if one or both of the outermost drug releasing layers degrades, the underlying layer will have a similar anchoring or anti-adhesion effect as the respective overlying layer(s). Thus, the anchoring effect or the anti-adhesive effect of the respective surface(s) of the prosthesis will not essentially be changed with the degradation of the drug-releasing layer.

In the context of the present invention, the term "drug" generally means a therapeutic or pharmaceutical agent which can be mixed into the polymer composition of any of the above-mentioned drug-releasing layers, or impregnated or incorporated into the polymer layer in order to provide a drug-containing polymer layer. The drug in the drug-containing coating can be any therapeutic or pharmaceutical agent suitable for use in drug-containing layers for implantable prosthesis. Various examples include, but are not limited to: anti-inflammatory agents such as adrenocortical steroids (cortisol, cortisone, corticosterone, budenoside, estrogen, sulfasalazine, mesalamine, fludrocortisone, prednisone, prednisolone, 6-alpha-methylprednisolone, triamcinolone, betamethasone, and dexamethasone), non-steroidal agents (such as salicylic acid derivatives, e.g., aspirin); analgetic agents such as paracetamol (acetaminophen), non-steroidal anti-inflammatory drugs (NSAIDs) (e.g., salicylates like aspirin, ibuprofen, and naproxen), narcotic drugs (e.g., morphine), synthetic drugs with narcotic properties (e.g., tramadol); immunosuppressive or immunodepressive agents (such as cyclosporine, tacrolimus (FK-506), sirolimus (rapamycin), azathioprine, mycophenolate mofetil); wound healing or scar formation preventing agents such as angiogenic agents like vascular endothelial growth factor (VEGF), fibroblast growth factors (FGF, PDGF, TGF-β); adhesion-promoting agents promoting or encouraging adhesion or attachment of endothelial cells to a surface including endothelial cell growth factors (e.g., platelet-derived ECGF, ECGF-β, 'ECGF-2a or ECGF-2b); anti-microbial agents such as triclosan or cephalosporins, or an anti-microbial peptide such as a magainin, aminoglycoside or nitrofurantoin; cytotoxic agents, cytostatic agents or cell proliferation affectors; vasodilating agents or agents that interfere with endogenous vasoactive mechanisms; anti-restenotic agents such as antiproliferative/antimitotic agents including natural products such as vinca alkaloids (e.g., vinblastine, vincristine, and vinorelbine), paclitaxel, epidipodophyllotoxins (e.g., etoposide, teniposide), antibiotics (dactinomycin (actinomycin D), daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiproliferative/antimitotic alkylating agents such as nitrogen mustards (such as mechlorethamine, cyclophosphamide and analogs, melphalan, chlorambucil), ethylenimines and methylmelamines (hexamethylmelamine and thiotepa), alkyl sulfonates-busulfan, nirosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (e.g., estrogen); anticoagulants (heparin, synthetic heparin salts and other inhibitors of thrombin); fibrinolytic agents (such as tissue plasminogen activator, streptokinase and urokinase); antiplatelet (such as aspirin, dipyridamole, ticlopidine, clopidogrel, abciximab); antimigratory; antisecretory (such as breveldin); para-aminophenol derivatives (e.g., acetaminophen); indole and indene acetic acids (such as indomethacin, sulindac, and etodalac), heteroaryl acetic acids (such as tolmetin, diclofenac, and ketorolac), arylpropionic acids (such as ibuprofen and derivatives), anthranilic acids (such as mefenamic acid, and meclofenamic acid), enolic acids (such as piroxicam, tenoxicam, phenylbutazone, and oxyphenthatrazone), nabumetone, gold compounds (such as auranofin, aurothioglucose, gold sodium thiomalate); nitric oxide donors; anti-sense oligo nucleotides and combinations thereof.

In some embodiments, the drug is a protein which is selected from an antibody or antibody binding fragment thereof, a growth factor such as an anti-microbial growth factor, and/or a cardiovascular therapeutic protein. Another example of a drug that may be used in the prosthesis is a small chemical molecule selected from an anti-inflammatory agent, an analgetic agent, an anti-microbial agent, a wound-healing or scar formation preventing agent, and/or an anti-restenotic or immunodepressive agent.

In this context, it is noted that the drug (therapeutically or pharmaceutically active agent) to be incorporated into one or more of the layers of the coating can be a small organic or chemical molecule, a protein or a fragment of the protein, a peptide or a nucleic acid such as DNA or RNA or any combination thereof. The term "small chemical molecule" as used herein typically denotes an organic molecule comprising at least two carbon atoms, but preferably not more than 7 or 12 rotatable carbon bonds, having a molecular weight in the range between 100 and 2000 Dalton, or between 100 and 1000 Dalton, that optionally can include one or two metal atoms. The term "peptide" as used herein typically refers to a dipeptide or an oligopeptide with 2-about 40, 2-about 30, 2-about 20, 2-about 15, or 2-about 10 amino acid residues. The peptide may be a naturally occurring or synthetic peptide and may comprise—besides the 20 naturally occurring L-amino acids, D-amino acids, non-naturally occurring amino acids and/or amino acid analogs. Specific examples of synthetic peptides are arginine-glycine-aspartate (RGD), arginine-glutamic acid-aspartic acid-valine (REDV), and tyrosine-isoleucine-glycine-serine-arginine (YIGSR). With "protein" is meant any naturally occurring polypeptide that comprises more than 40 amino acid residues. The protein can be a full length protein or a truncated form, for example, an active fragment. Illustrative examples of proteins include, but are not limited to antibodies, antibody binding fragments thereof or other binding proteins with antibody like properties (for example, affibodies or lipocalin muteins knows as "Anticalins®") for selected cell receptors; vascular growth inhibitors such as inhibitory antibodies, antibodies directed against growth factors, bifunctional molecules consisting of a growth factor and a cytotoxin, bifunctional molecules consisting of an antibody and a cytotoxin; growth factors such as VEGF (Vascular Endothelial Growth Factor) and similar factors for transmitting signals, cardiovascular therapeutic proteins or cardiac hormones and active fragments thereof or prohormones or preprohormones of such cardiac hormones (these hormones or the prohormones can either be peptides as defined herein, if they have less than 40 amino acid residues, or proteins, should their polypeptide sequence contain more the 40 amino acid residues). Further examples for cardiovascular therapeutic agents can be peptides or DNA such as the DNA for nitric oxide. Examples of nucleic acid molecules include sense or anti-sense DNA molecules (if expression of a target gene is to be controlled) or the coding sequence (either alone or in gene-therapy vector, for example) of a therapeutically active protein that is to be produced. In such a case, the nucleic acid may code for a protein that promotes wound healing as described, for example, in WO 97/47254.

The amount of the drug (or 2 or more drugs together) in one or more layers of the coating is not limited and can be as high as wanted as long as the physical properties of the polymer layer, especially the burst strength, the flexibility, the glass transition temperature or the elongation at break are not adversely affected. In some embodiments, the amount of the drug, based on the dry weight of the polymer layer that contains the drug, may be up to about 35 wt %. The drug may be present in an amount of 0.1 to 35 wt %, 1 to 35 wt % or 1 to 10, 15, 20, 25 or 30 wt % based on the dry weight of the polymer layer that contains the drug.

In some embodiments, the prosthesis is provided with memory effect properties. The memory effect allows the multi-layered structure to reshape itself to a desired contour (i.e., having a shape memory effect). The material returns from a deformed state (temporary shape) to its original (permanent) shape induced by an external stimulus, such as, e.g., temperature change. This memory effect can for instance be used to place the implant into the correct position during surgical implantation by using a minimally invasive (trough small incisions or natural orifices) implantation technique. The prosthesis is placed at the desired site within the body in its small temporary shape, which, after activating the shape memory by, e.g., temperature increase, reshapes into its permanent (and mostly bulkier) shape. Thus, the incision can usually be made smaller or can be minimized. In addition, when memory effect prosthesis are used for instance in surgical sutures, the shape memory property of material used enables wound closure with self-adjusting optimal tension, which avoids tissue damage due to too tight sutures and does support healing and/or regeneration.

Figure 6:
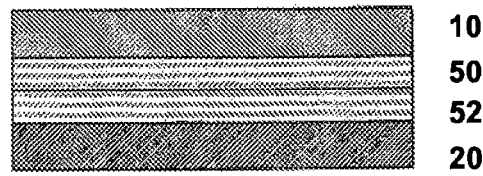
FIG. 6 shows another embodiment of a prosthesis comprising two memory-effect providing layers 50 and 52 located or arranged between the porous layer 10 and the reinforcing layer 20.

The memory effect properties can be provided by any of the layers 10, 20, 30, 40, or 42 as discussed above, or by adding two additional memory-effect providing layers (50; 52) into the multi-layered structure. Thereby it is needless to say that these layers can be provided as two adjacent layers or at different sites of the multi-layered structure. In an exemplary embodiment, which is shown in FIG. 6 (this is only one of various possible embodiments), the two memory-effect providing layers 50 and 52 are, for instance, arranged between the porous layer 10 and the reinforcing layer 20, which can have at the same time anti-adhesion properties. In other examples, both layers can for example be provided in a three- or five-layered prosthesis shown in FIG. 4 or 5. In order to be able to maintain the respective properties of the drug-releasing or surface-treated outermost layers, the memory-effect providing layers 50 and 52 are usually provided instead or adjacent to the reinforcing layer.

The memory-effect providing layers can be of any material having a sufficient memory effect such as Shape Memory Polymers (SMPs). SMPs are polymeric materials which have the ability to return from a deformed state (temporary shape) to their original (permanent) shape induced by an external stimulus, such as, e.g., temperature change. Various SMPs are thermoplastic and thermoset (cross-linked) shape memory polymers such as polymers or copolymers of, e.g., polylactic acid, polyglycolic acid, polycaprolactone. Those polymers and copolymers are well-established in the medical device technology field. Usually, the SMPs should be biocompatible in order to avoid any toxic or irritating adverse effect.

An illustrative example for a two-layered structure having memory effect is a layer 50 made of a poly(lactide) and poly(glycolide) co-polymer (PLGA) having a poly(lactide) and a poly(glycolide) content of about 50%, respectively, and a layer 52 made of a poly(lactide) and poly(glycolide) co-polymer (PLGA) having a poly(lactide) content of about 75% and a poly(glycolide) content of about 25%.

In some embodiments, the prosthesis having a multi-layered sheet structure has an anisotropic pore structure or the pores have an anisotropic shape. These anisotropic structures allow that the prosthesis of the invention can be adapted to the anisotropic nature of a site at which the prosthesis is to be inserted. More particularly, the flexibility and burst strength of the prosthesis can be sufficiently and variably controlled by the specific novel anisotropic pore structure to obtain improved fixation and incorporation of the prosthesis for instance to the surrounding musculo-aponeurotic layer or the surrounding tissue.

Illustrative anisotropic structures which provide the above-mentioned advantages and can be readily prepared by the methods of the present invention are shown in the FIGS. 8, 9, and 11 to 13.

Figure 7:
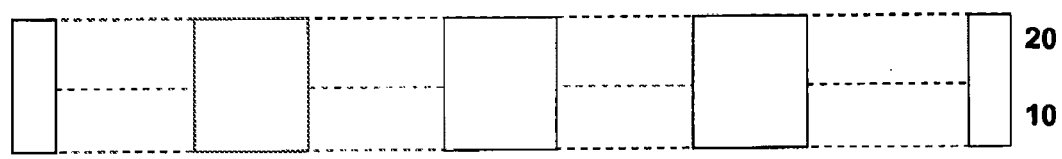
FIG. 7 is a cross sectional view of an embodiment of the prosthesis shown in FIG. 3 having non-tapered through-holes extending through the prosthesis.
Figure 8:
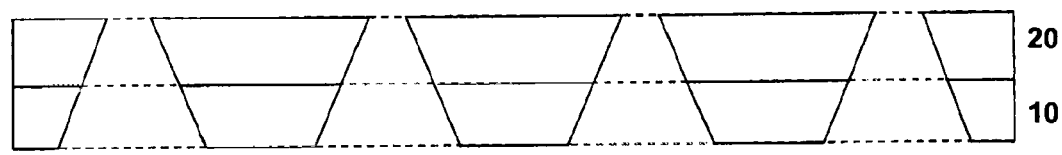
FIG. 8 is a cross sectional view of another embodiment of the prosthesis shown in FIG. 3 having tapered through-holes extending through the prosthesis.

FIG. 8 is a cross sectional view of an embodiment of the prosthesis shown in FIG. 3 (a two-layered prosthesis) having tapered through-holes (shown by dashed lines) extending through all layers of the prosthesis. It is needless to say that such a pore structure can be applied to all of the aforementioned multi-layered structures such as prosthesis with three, four or more different layers. The cross-sectional shape of such pores can be any regular or irregular shape such as a circular, elliptical, oval, polygonal shape (e.g., a triangular, square, pentagonal or rhomb-like shape), non-circular cross-section or a monosymmetric shape. As described above, the structure of the surfaces of the wall can also be irregularly shaped in order to enhance the surface friction. In contrast to the prosthesis shown in FIG. 7 having a straight shape of the through holes (shown by dashed lines), the penetration or growth in of tissues into the pores can be controlled by the specific anisotropic pore shape (the tapered shape, e.g., a conical or pyramidal shape). In addition thereto, the pore size on the surface of the reinforcing layer 20 may be adjusted into a sub-micrometer range so that any tissue penetration can be essentially prevented. The small holes on the surface of the reinforcing layer 20, however, can at the same time allow the elution of drugs, for example.

Figure 9:
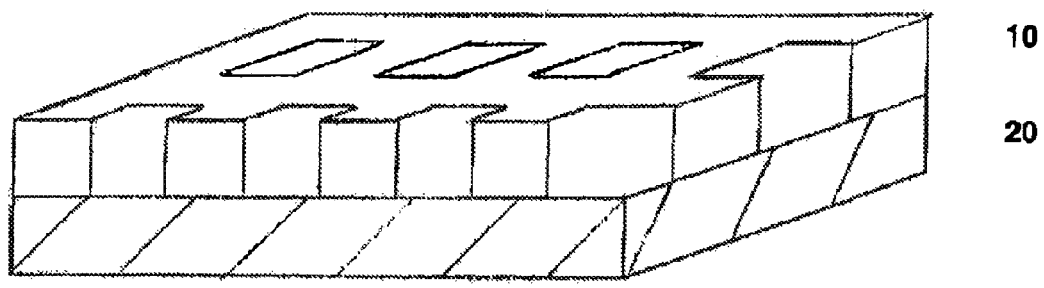
FIG. 9 is a perspective view of a further embodiment of the prosthesis shown in FIG. 3 having through-holes extending through the porous layer of the prosthesis.

FIG. 9 is a perspective view of a further embodiment of the prosthesis shown in FIG. 3 (having a two-layered structure). In this exemplified embodiment, the pores are formed as through-holes through the porous layer of the prosthesis only. This also facilitates the growth in of abdominal tissues into the porous layer 10, for example, while at the same time, the reinforcing layer 20 acts as a blocking or barrier layer for the tissue. In this specific embodiment the pores have a square-like shape.

Figure 10:
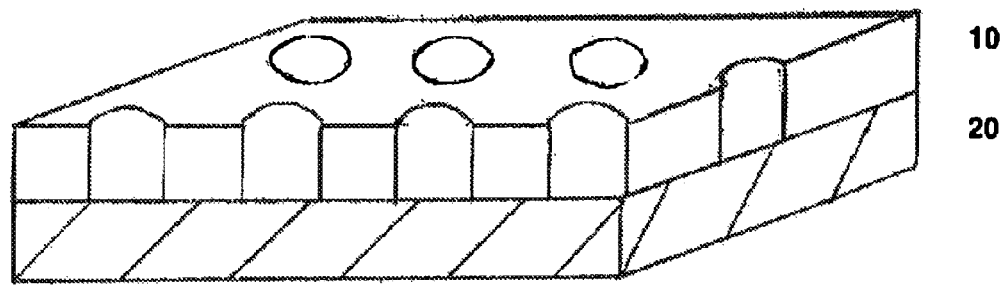
FIG. 10 is a perspective view of another embodiment of the prosthesis shown in FIG. 3 having through-holes extending through the porous layer of the prosthesis.

FIG. 10 is a perspective view of another embodiment of the prosthesis shown in FIG. 3 also having through-holes extending through the porous layer (10) of the prosthesis only. In this embodiment the pores have a cylindrical shape.

Figure 11A:
FIGS. 11a-c are cross sectional views of three different embodiments of the prosthesis shown in FIG. 3, wherein the prosthesis in FIG. 11a has a roughed surface and the prosthesis in FIG. 11b has a tapered pore form and the prosthesis in FIG. 11c has a sac-like pore structure.
Figure 11B:
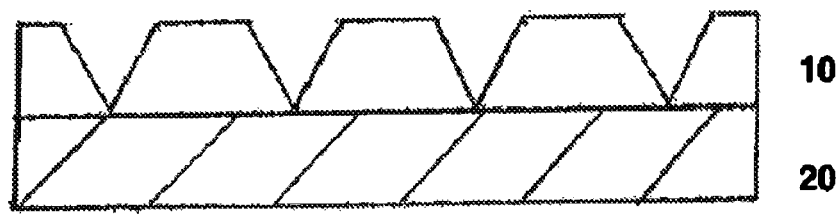
Figure 11C:
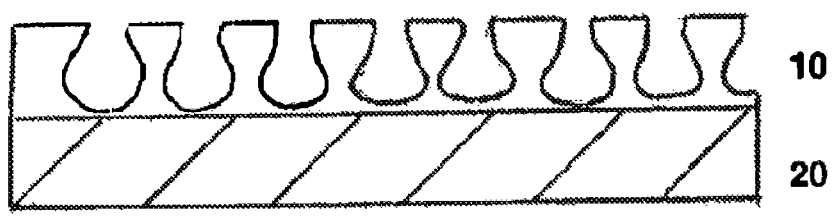

It is to be noted here that the prosthesis of the present invention is not limited to the two illustrative examples shown in FIGS. 9 and 10. One skilled in the art knows various shape designs in which the pores can be formed. Various illustrative examples of such pore structures (extending within the porous layer 10, but can also be extended within one, two or more layers of the multi-layered structure or can be through holes extending through the prosthesis) are shown in FIGS. 11a, 11b, and 11c, for example. Each illustrated embodiment, such as the roughed surface shown in FIG. 11a having cavities or depressions in the surface area only, the tapered pore form shown in FIG. 11b having a conical or pyramidal shape, for example, or the sac-like pore shape shown in FIG. 11c is suitable for providing a controlled anisotropic pore structure to ensure a better fixation and incorporation of the prosthesis for instance to the surrounding musculo-aponeurotic layer or the surrounding tissue. One skilled in the art can find additional pore anisotropic pore shapes by routine experimentation.

Figure 12A:
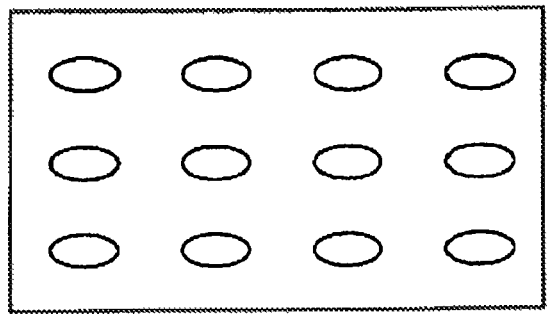
FIGS. 12a-c are plane views of various embodiments of a prosthesis having anisotropic pore shapes.
Figure 12B:
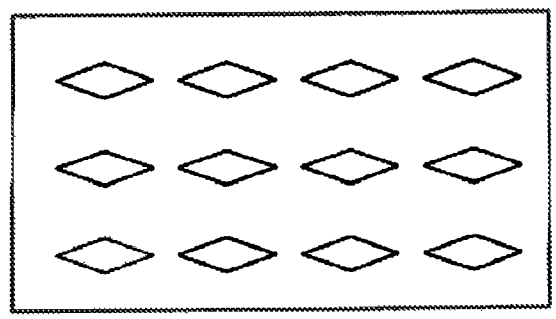
Figure 12C:
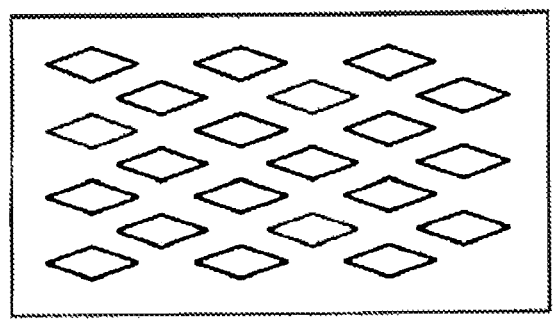
Figure 13A:
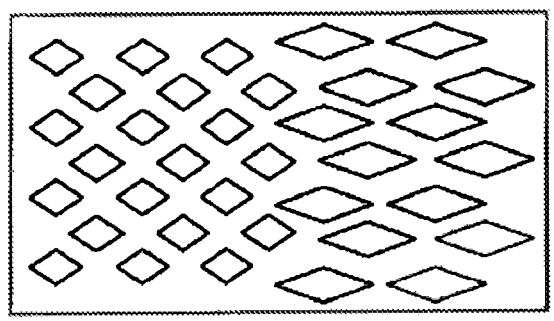
FIGS. 13a-b are plane views of various embodiments of the prosthesis of the invention having anisotropic pore structures.
Figure 13B:
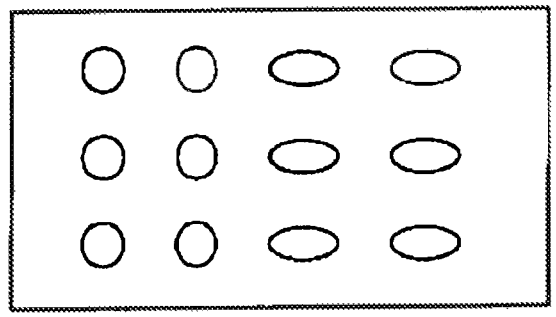

FIGS. 12a-c and 13a-b show further illustrative embodiments of a prosthesis having an improved anisotropic pore shape or pore structure. FIGS. 12a-c are plane views of various embodiments of a prosthesis having anisotropic pore shapes. FIGS. 13 a-b are plane views of various embodiments of a prosthesis having anisotropic pore structures. For example in FIG. 13a, the pores on the left side of the prosthesis have a square shape, while the pores on the right side have a rhomb-like shape, while the longitudinal axis has not been changed. Similarly, the pore shape changes from the left side to the right side in the prosthesis shown in FIG. 13b. In this embodiment, the shape varies from a circular one to an oval shape. Several possibilities of varying the shape of coplanar pores or mixing different shapes can be made by one skilled in the art by routine experimentation in order to design a specific controlled pore structure having anisotropy sufficient to better copy or simulate the anisotropic anatomical nature of the surrounding tissue.

It is noted that all these pore shapes cannot be made by any weaving or knitting technique as described in the prior art discussed above, so that these specific novel anisotropic pore shapes and their effects on the anisotropy of the prosthesis are unique in the art in the field of surgical prosthesis.

Figure 14:
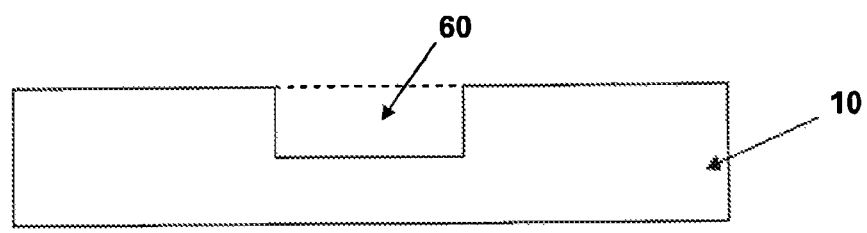
FIG. 14 is a sectional view of a porous layer 10 of an alternative embodiment of the prosthesis of the invention having pores in its surface layer in the form of wells or pot holes 60.

An alternative embodiment is shown in FIG. 14. In this embodiment a porous layer 10 comprising pores in its surface layer in the form of wells or pot holes 60 is shown. The other layers like a reinforcing layer 20, etc., are not shown in this figure. The film thickness of the porous layer is, e.g., about 500 µm, and wells or pot holes 60 can be cut into the porous layer, e.g., by using laser cutting, embossing, or drilling. In this case, the wells or pot holes 60 do not penetrate the porous layer because the depth of the holes 60 is less than the thickness of the porous layer. In the embodiment shown in FIG. 14, the thickness is, e.g., about 300 µm. In other parts of the prosthesis in which no wells or pot holes 60 are provided, pores such as trough holes perforating the porous layer or the whole prosthesis can be provided (not shown in the Figure) as described above. Thus, the prosthesis of this embodiment can have two different pores, namely the through holes and the holes 60. The holes 60, i.e., the wells or pot holes, can be used to induce cell regeneration, for example. In order to induce cell regeneration, the wells or pot holes can contain additives such as drugs, proteins, etc., as described above or they can simply act as cavity sites for cell regeneration.

In the second aspect of the invention, a method of manufacturing a prosthesis having a multi-layered sheet structure is provided. The method comprises steps of forming two continuous polymer film layers to produce the multi-layered sheet structure.

In this respect, it is reminded that any layer of the prosthesis is made from a polymeric material in the form of a continuous film. Furthermore, the continuous polymer film layer is usually made from a liquid or paste-like polymer material, followed from hardening the material in order to generate a continuous polymer film. In some embodiments, the at least two layers are formed, for example, by molding methods like injection molding and compression molding; coating methods like solution coating, dip coating or spin coating; solution casting; and/or an extrusion method like blow extrusion or film extrusion.

In case a casting method is used, the polymer film can be interrupted by pores or through-holes during the manufacturing of the polymer film layer by using a specific mold having matrix pattern for the pores. For example, a roughed surface can be provided by using a roughened mold. Similarly, any pore structure such as a mesh-like structure can be easily made by injection molding techniques if a respective two-part or multi-part mold is used.

In alternative embodiments, various mechanical or chemical treatments can be used for treating the multi-layered structure or one, two or more of these layers or the surface of the outermost layers. Exemplary embodiments of mechanical treatments are mechanical abrading or cutting methods, such as stamping, grinding, laser cutting, electrical discharge machining, drilling and the like. By these methods the respective polymer layers treated at the desired region can easily be formed into a porous or mesh-like structure.

In another exemplary embodiment, the friction of a roughed surface, which can for example be prepared by casting on a roughened mold, followed by layering the other layers of the multi-layered structure thereon, can for instance be suitably adjusted by means of a treatment for altering the surface of the pores or the porous layer. Such a treatment may include various means, such as mechanical, thermal, electrical, or chemical means. Various examples of a mechanical treatment suitable for adjusting the desired surface friction and/or surface roughness of the layer include, but are not limited to, a plasma treatment, a sandblasting treatment, an embossing treatment, or a sizing treatment. Various examples of a chemical treatment include a plasma polymerization coating or solution coating or a chemically etching treatment. As an illustrative example of a chemical surface treatment for increasing the wetting ability, for example, can be mentioned a treatment for rendering the surface properties of any hydrophobic surface hydrophilic by coating with a hydrophilic polymer or by treating for instance with surfactants.

The above-described solvent cast multi layered film process helps to overcome the limitations of the current filament woven mesh processes as the film will after its manufacturing be laser cut. Laser cutting opens up all possibilities of designs including the anisotropic design that would optimally match the anisotropic anatomical nature of the abdominal wall. Thus, the prosthesis generally is cut from a flat multilayered sheet by laser cutting, using a design which has been computationally analyzed (e.g., by Finite Element Analysis, FEA; generally using an iterative process) beforehand to give the anisotropic properties desired. The same method can also be used to achieve a design using a minimal amount of materials. Therefore, material costs can be lowered and the manufacturing process can be made more cost efficient. In addition, in line with the so-called Halstead's principle, the least amount of foreign body introduced to patients, the better they are. In hernia repair, it equates to having the least amount of material with optimum strength for permanent support. Using this principle, the design of the pores and the thickness of the prosthesis can satisfactorily be adjusted by the above-described method.

All these methods easily allow the fabrication of a controlled pore structure. For example, pores having an irregular shape like a non-circular or monosymmetric shape or pore structures with an anisotropic structure can be manufactured by these methods. It is needless to say that regular pore structures can also be manufactured by these methods. Since the different pore shapes have already been described in detail with respect to the prosthesis it will not be repeated here. One skilled in the art knows how to produce the respective shape by using one of the above-mentioned methods.

In another exemplified embodiment, the outermost layer of a multi-layered structure is made by dispersing inorganic or organic fine particles and/or inorganic/organic composite particles in the polymer mixture and then molding the respective layer to obtain a roughened surface. Various examples include, for example, inorganic particles such as silica, titania, bentonite, clays or mixtures thereof; organic particles such as oligomers or polymers having a melting point higher than the polymer of the polymeric film; or inorganic/organic composite particles such as particles of silica or titania as core material and having a polymeric shell. Thus, a roughed surface having improved surface friction properties can be provided. If needed, the obtained rough surface can be after-treated as described above in order to further improve the friction or wettability of the surface.

As described above, the method comprises in exemplary embodiments the forming of an anti-adhesion coating layer on at least a part of one or both outer surface(s) of the prosthesis, where the respective coating is desired. The method can also encompass the step of providing drug releasing layer(s) or memory effect-providing layers.

In the following, illustrative working examples of manufacturing methods of a multi-layer prosthesis are described, wherein these examples are not intended to limit the present invention to these three embodiments. In all examples polyvinylidene fluoride (PVDF) is used as polymer material of the multi-layered prostheses. The Applicant has developed these novel methods to cast multiple layers of PVDF which has been shown to be fully biocompatible. PVDF has higher strength and yet retains good flexibility. This allows the prosthesis to be made thinner than current polypropylene mesh prostheses. It also retains these properties very well and does not form cracks over time when embedded in the body, which were the key problems in polypropylene mesh. It is highly resistant to hydrolysis and has minimal shrinkage. This is a further strong improvement over a conventional PTFE mesh.

(1) Solution Casting:

According to this method the polymer material was first dissolved into a suitable solvent. In those layers containing drugs, drugs were first dissolved in the polymer solution before being casted. The solution was then applied onto a mold where the surface profile determined the surface roughness or profile of the first layer. The contour of the mold was also the shape of the final desired contour when the film has been implanted. The layer was then dried carefully to release all the solvents before the next layer was similarly deposited. This process was repeated iteratively until the desired number of layers had been achieved. The whole multi layered film was then heat treated above glass transition temperature of one or more polymer layers on the mold to obtain the formation of a prosthesis in the desired shape. The contoured film was then flattened at 25° C. or below into a flat sheet before insertion into the body. The film will then revert to its desired contoured shape at 37° C. once placed into the body.

(2) Dip Coating:

The multi layered film was casted by dip-coating the mold vertically and in a controlled manner into a solution of a polymer and lifting it up with the polymer layer coating on the mold. In those layers the drugs were first dissolved in the polymer solution before being casted. The coating was then dried to release all the solvents before dip coating into another polymer solution to achieve the second layer. The process was then repeated iteratively until the desired layers had been obtained. The mold had a surface profile determining the surface roughness or profile of the first layer. The contour of the mold resembled the shape of the final desired contour obtained after implantation of the film. The whole multi layered film was then heat treated above glass transition temperature of one or more polymer layers on the mold to obtain the formation of the desired shape. The contoured film was then flattened at 25° C. or below into a flat sheet before insertion into the body. The film will then revert to its desired contoured shape at 37° C. once placed into the body.

(3) Spin Coating:

Spin coating employs a method where the polymer solution is applied drop by drop on a fast spinning mold to obtain an even spun coating on the mold. This method was used for the desired polymer materials. In those layers containing drugs, drugs were first dissolved in the polymer solution before being casted. The contour of the mold also resembled the shape of the final desired contour obtained after implantation of the film. The layer was then dried carefully to release all the solvents before the next layer was deposited on the previous layer in the same manner. This process was repeated iteratively until the desired number of layers had been achieved. The whole multi layered film was then heat treated above glass transition temperature of one or more polymer layers on the mold to obtain the desired shape. The contoured film was then flattened at 25° C. or below into a flat sheet before insertion into the body. The film will then revert to its desired contoured shape at 37° C. once placed into the body.

(4) Alternative Manufacturing Methods:

Similar PVDF films were prepared by molding or extrusion methods instead of the above-described casting methods. After having molded the film, a specific pore pattern was cut by using laser cutting or mechanically cutting (e.g., drilling), thus providing a mesh-like film structure.

The thus obtained film structure was then further processed by adhering a top coating made of carboxymethylcellulose (other biodegradable materials can also be used in the same manner) containing pharmaceutically active agents thereon. In order to enhance the adhesive properties, biocompatible polymers like PLGA were used as adhesive-promoting agents in the form of an additional film or as adjective to the carboxymethylcellulose. Thus, a multi-layered film prosthesis was prepared comprising a porous PVDF film layer.

Another aspect of the invention refers to methods of treating a patient by implanting the prosthesis according to the present invention. The method according to the third aspect of the invention generally encompasses the step of implanting the prosthesis of the invention as described beforehand into a mammal such as a human, dog, cat, rabbit, mouse, rat, etc.

In some embodiments, the method (or the prosthesis) can be used for treating any wall defect or damaged organ, but is not limited thereto. Various examples of wall defects are hernia defects, anatomical defects of the abdominal wall, diaphragm and/or chest wall, or defects in the genitourinary system. Various examples of damaged organs which can be treated, for example, by winding the sheet-like prosthesis around the damaged organ or implanting it into the wall of the damaged organ for reinforcing it, include internal organs such as the spleen, liver, kidney, lung, bladder or heart, or organs of the intestinal tract such as the stomach or the bowel. Illustrative examples of the method include the implantation of a prosthesis, such as heart patches, colonic patches, vascular prosthesis like vascular patches, patches for wound healing like suture patches or meshes, hernia patches, gastrointestinal prosthesis like prosthesis for the mouth, pharynx, esophagus, stomach, small intestine, large intestine, rectum, and anus, patches for the urogenital system and the like.

In conclusion, it has been shown by the above description that a prosthesis can be made perfectly compliant with the surrounding tissue and move in line with these tissues. In addition, a prosthesis can adequately anchor to the surrounding tissue and be able to flexibly and elastically stretch along with the tissue due to their unique pore structure, especially the anisotropic pores or anisotropic pore structures. Therefore, the novel prostheses can overcome most of the disadvantages of the conventional prostheses, which generally would not anchor well or are not flexible (such as the conventional hernia meshes made of several polymeric filaments or fibers) and, thus, slide painfully against the patient abdominal tissues. This sliding generally causes great discomfort and even trauma against the abdomen.

In addition, the prosthesis of the invention do not allow itself to develop tissue adhesions with the viscera because of the possibility of providing each layer of the multi-layered structure with different properties such as an anti-adhesion property of the layer facing the visceral tissue. Since visceral adhesions generally result in postoperative pain, intestinal obstruction, and most seriously, fistula formation, the novel prosthesis of the present invention overcome these disadvantages of the conventional prosthesis at the same time.

Moreover, the present invention provides a novel drug-releasing multi-layer prosthesis for, e.g., reinforcement of abdominal wall in mammals or repairing other defects in walls or organs. To avoid unintended connection to visceral tissue or internal organs a prosthesis is provided in which one side of the prosthesis comprises a non-adhesive function and the other side comprises a higher friction and adhesive function to promote anchoring of the prosthesis to tissue or organ surfaces. This prosthesis can also be used in other surgical procedures including the repair of anatomical defects of the abdominal wall, diaphragm, and chest wall, correction of defects in the genitourinary system, and repair of traumatically damaged organs such as the spleen, liver or kidney.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of manufacturing a prosthesis having a multi-layered sheet structure, comprising integrally forming at least two continuous polymer film layers with no distinguished filaments or fibers within each layer, wherein the at least two continuous polymer film layers are in continuous contact with each other to produce the multi-layered sheet structure, and wherein the outermost layer of the multi-layered sheet structure is formed by casting the polymer on a roughened mold to obtain a roughed surface, forming the additional layers thereon and, then, mechanically or chemically treating said roughed surface to increase its surface friction and wetting ability.

2. The method according to claim 1, wherein the at least two layers are formed by at least one method selected from the group consisting of: molding methods; coating methods; solution casting; and an extrusion method.

3. The method according to claim 1, wherein the mechanical treatment of the roughed surface includes a plasma treatment, a sandblasting treatment, an embossing treatment, or a sizing treatment.

4. The method according to claim 1, wherein the chemical treatment of the roughed surface comprises an etching treatment or a coating.

5. The method according to claim 1, wherein pores are made in one or more layers of the multi-layered structure by using a matrix having a pore pattern.

6. The method according to claim 1, wherein a porous layer is formed in the form of a solid layer as an outermost layer and then the porous structure is formed from this solid layer by means of a mechanical treatment.

7. The method of claim 6, wherein the mechanical treatment is a grinding process, a laser cutting process, an electrical discharge machining, stamping or a mechanical abrading process.

8. The method according to claim 1, wherein an anti-adhesion coating layer is formed on at least a part of one or both outer surface(s) of the prosthesis.

9. The method according to claim 8, wherein the anti-adhesion coating layer comprises a biocompatible or bioresorbable polymer.

10. The method according to claim 8, wherein the anti-adhesion coating layer comprises an anti-adhesion agent.

11. The method according to claim 1, wherein the multi-layered structure is made of at least two layers comprising a biocompatible or bioresorbable polymer material.

12. The method according to claim 11, wherein the biocompatible polymer material is any of polyvinylidene fluoride, polyamide, polyethylene, polypropylene, poly(ethylene terephtalate), polyurethane, polystyrene, polymethacrylate, polytetrafluoroethylene, and polymers or copolymers of p-dioxanone, trimethylene carbonate and alkyl derivatives thereof, valerolactone, butyrolactone, decalactone, hydroxybutyrate, hydroxyvalerate, 1,5-dioxepan-2-one, 1,4-dioxepan-2-one, 6,6-dimethyl-1,4-dioxan-2-one or any polymer blend thereof.

13. The method according to claim 11, wherein the bioresorbable polymer material is any of polyglycolide, polylactide and poly-co-glycolactide, polylactic acid, polyglycolic acid, poly(ethylene glycolide), polyethylene glycol, polycaprolactone like poly(c-caprolactone), polydioxanone, polygluconate, polylactic acid-polyethylene oxide copolymers, polysaccharides, cellulose derivatives, hyaluronic acid based polymers, starch, gelatin, collagen, polyhydroxybutyrate, polyanhydride, polyphosphoester, poly(amino acids) or any polymer blends, copolymers, or derivatives.

14. The method according to claim 1, wherein at least one layer is provided with pores having an average pore size of about 0.5-5 mm.

15. The method according to claim 1, wherein at least one layer is provided with pores having an average pore size of about 1-4 mm.

16. The method according to claim 1, wherein at least one layer is provided with pores having a regular or irregular shape.

17. The method according to claim 16, wherein the pores having a regular shape have a circular, elliptical, oval or polygonal shape such as a triangular, square, pentagonal or rhomb-like shape.

18. The method according to claim 16, wherein the pores having an irregular shape have a non-circular cross-section or a monosymmetric shape to provide an anisotropic pore structure.

19. The method according to claim 16, wherein coplanar pores in the multi-layered structure have different pore diameters or pore shapes to provide an anisotropic pore structure.

20. The method according to claim 1, wherein at least one layer is provided with pores having an anisotropic shape in its cross-section.

21. The method according to claim 20, wherein the anisotropic shape of the pores tapers from the upper surface of the porous layer to the inner part thereof or the opposite side of the prosthesis.

22. The method according to claim 16, wherein the anisotropic pore structure or the anisotropic shape of the pores is adapted to the anisotropic anatomical nature of a site at which the prosthesis is to be inserted in a patient.

23. The method according to claim 1, wherein one, two, or more of the layers of the multi-layered structure like the porous layer or the anti-adhesion coating layer are made as drug-releasing layers by adding one or more compounds selected from the group consisting of: releasable drugs, therapeutic agents, and pharmaceutically active substances in the respective layers before molding the layers or by impregnating them into the molded layers.

24. The method according to claim 1, further comprising the step of forming an additional polymeric drug-releasing layer on one or both outermost layers of the prosthesis, comprising one or more compounds selected from the group consisting of: releasable drugs, therapeutic agents, and pharmaceutically active substances.

25. The method according to claim 1, wherein two layers in the multi-layered sheet structure are formed to provide a memory effect.

26. The method according to claim 25, wherein these two layers are formed of a polymeric material as two additional layers providing the memory effect properties in the multi-layered sheet structure of the prosthesis.

27. The method according to claim 1, wherein the at least two layers are formed by at least one technique selected from the group consisting of: injection molding, compression molding, dip coating, spin coating, blow extrusion, and film extrusion.

28. The method according to claim 1, wherein the chemical treatment of the roughed surface comprises a plasma polymerization coating or solution coating.

* * * * *